(12) United States Patent
Miyahara et al.

(10) Patent No.: US 7,888,013 B2
(45) Date of Patent: Feb. 15, 2011

(54) METHOD OF ANALYZING DNA SEQUENCE USING FIELD-EFFECT DEVICE, AND BASE SEQUENCE ANALYZER

(75) Inventors: Yuji Miyahara, Ibaraki (JP); Toshiya Sakata, Ibaraki (JP)

(73) Assignee: National Institute for Materials Science, Tsukuba-shi (JP)

( * ) Notice: Subject to any disclaimer, the term of this patent is extended or adjusted under 35 U.S.C. 154(b) by 670 days.

(21) Appl. No.: 11/574,353

(22) PCT Filed: Aug. 26, 2005

(86) PCT No.: PCT/JP2005/015522

§ 371 (c)(1),
(2), (4) Date: Aug. 6, 2007

(87) PCT Pub. No.: WO2006/022370

PCT Pub. Date: Mar. 2, 2006

(65) Prior Publication Data

US 2008/0286767 A1    Nov. 20, 2008

(30) Foreign Application Priority Data

Aug. 27, 2004    (JP) ............................. 2004-248258

(51) Int. Cl.
C12Q 1/68 (2006.01)
C07H 21/02 (2006.01)
C07H 21/04 (2006.01)
(52) U.S. Cl. ..................... 435/6; 536/23.1; 536/24.3
(58) Field of Classification Search ............. 435/6; 536/23.1, 24.3
See application file for complete search history.

(56) References Cited

U.S. PATENT DOCUMENTS

| | | | | |
|---|---|---|---|---|
| 4,777,019 A * | 10/1988 | Dandekar | ............... | 422/82.02 |
| 5,466,348 A * | 11/1995 | Holm-Kennedy | ........... | 205/775 |
| 6,361,671 B1 * | 3/2002 | Mathies et al. | .............. | 204/452 |
| 6,475,728 B1 * | 11/2002 | Martin et al. | .................. | 435/6 |
| 6,939,451 B2 * | 9/2005 | Zhao et al. | ................... | 204/451 |
| 7,169,560 B2 * | 1/2007 | Lapidus et al. | ................. | 435/6 |
| 7,297,518 B2 * | 11/2007 | Quake et al. | ............... | 435/91.2 |
| 2002/0086318 A1 * | 7/2002 | Manalis et al. | ................. | 435/6 |
| 2003/0148301 A1 * | 8/2003 | Aono et al. | ..................... | 435/6 |
| 2003/0186262 A1 * | 10/2003 | Cailloux | ........................ | 435/6 |
| 2005/0266456 A1 * | 12/2005 | Williams et al. | .............. | 435/6 |
| 2006/0057604 A1 * | 3/2006 | Chen et al. | ..................... | 435/6 |
| 2006/0154399 A1 * | 7/2006 | Sauer et al. | ................... | 438/48 |
| 2007/0138132 A1 * | 6/2007 | Barth | .......................... | 216/56 |
| 2008/0096216 A1 * | 4/2008 | Quake | ........................... | 435/6 |

FOREIGN PATENT DOCUMENTS

| | | | |
|---|---|---|---|
| JP | 8-278281 A | | 10/1996 |
| JP | 2002-272463 | * | 9/2002 |
| JP | 2003-533676 A | | 11/2003 |
| WO | WO01/42498 | * | 6/2001 |
| WO | 01/81896 A1 | | 11/2001 |

OTHER PUBLICATIONS

Fritz et al. Electronic detection of DNA by its intrinsic molecular charge. PNAS 99 (22) : 14142-14146 (2002).*
Li et al. Sequence-specific label-free DNA sensors based on silicon nanowires. Nano Letters 4 (2) : 245-247 (2004).*
Miyahara et al., "Potentiometric Detection of DNA Molecules Using Field Effect Transistor", The Japan Society of Applied Physics., No. 3, p. 1180,30a-S-2, 2003. English translation. cited in U.S. Appl. No. 10/587,941 now US 7,695,907.*
Miyahara et al., "Biochip Using Micromachining Technology", Journal of Institute of Electrostatics Japan, vol. 27, No. 6, pp. 268-272, 2003. English translation cited in U.S. Appl. 10/587,941 now US 7,695,907.*
Sakata et al.,Detection of DNA Hybridization by Genetic Transistor, The Japan Society of Applied Physics, No. 3, p. 1179, 30a-S-1, 2003. Englishtranslation cited in U.S. Appl. No. 10/587,941 now US 7,695,907.*
Sakata et al., Potentiometric Detection of DNA Molecules Using Genetic Field Effect Transistor, Denki Gakkai Kenkyukai Shiryo Chemical Sensor Kenkyukai, pp. 1-5, CH5-03-51-55, 2003. English translation cited in U.S. Appl. No. 10/587,941 now US 7,695,907.*
M. Ronaghi et al.; "A sequencing method based on real-time pyrophosphate", Science 1998, vol. 281, pp. 363-365.
A. Ahmadian et al.; "Single-nucleotide polymorphism analysis by pyrosequencing", Anal. Biochem. 2000, vol. 280, pp. 103-110.
Toshiya Sakata etal.; "Idenshi Transistor ni yoru-Enki Takei no Kenshutsu", Denki Gakkai Kenkyukai Shiryo Chemical Sensor Kenkyukai, May 12, 2004, CHS-04-01-13, pp. 45-50.

(Continued)

*Primary Examiner*—Ethan Whisenant
(74) *Attorney, Agent, or Firm*—Westerman, Hattori, Daniels & Adrian, LLP

(57) ABSTRACT

Since conventional DNA sequence analyzing technologies are based on the fundamental principle of fluorescent detection, expensive, complex optical systems and laser sources have been necessary.

A field-effect device for gene detection of the present invention analyzes a base sequence by immobilizing a single-strand nucleic acid probe at a gate portion, inducing hybridization at the gate portion to form a double-stranded DNA, inducing elongation reaction by adding a DNA polymerase and one of the substrates, and measuring the electrical characteristic of the field-effect device caused by elongation reaction.

Since the elongation reaction of one base induced at the gate portion can be directly converted to an electrical signal, expensive lasers or complex optical systems are not needed. Thus, a small gene polymorphism detection system that can conduct measurement at high precision can be provided.

5 Claims, 6 Drawing Sheets

OTHER PUBLICATIONS

Yuji Miyahara et al.; "Idenshi Transistor o Mochiita DNA Sequencing no Kento", Dai 27 Kai The Molecular Biology Society of Japan Program Koen Yoshishu, Nov. 25, 2004, vol. 27, p. 1024.

Toshiya Sakata et al.; "Idenshi Transistor o Mochata DNA Sequencing no Kento", Dai 65 Kai Oyo Butsuri Gakkai Gakujutsu Koenkai Koen Yokoshu, Sep. 1, 2004, No. 3, p. 1142.

International Search Report of PCT/JP2005/015522, date of mailing Sep. 27, 2005.

M. Ronaghi et al.; "A sequencing method based on real-time pyrophosphate", Science 1998, vol. 281, pp. 363-365.

A. Ahmadian et al.; "Single-nucleotide polymorphism analysis by pyrosequencing", Anal. Biochem. 2000, vol. 280, pp. 103-110.

Toshiya Sakata etal.; "Detection of Single Nucleotide Polymorphism Using Genetic Field Effect Transistor", Denki Gakkai Kenkyukai Shiryo Chemical Sensor Kenkyukai, May 12, 2004, CHS-04-01-13, pp. 45-50.

Yuji Miyahara et al.; "DNA Sequencing Using Genetic Field Effect Transistor" Dai 27 Kai The Molecular Biology Society of Japan Program Koen Yoshishu, Nov. 25, 2004, vol. 27, p. 1024.

Toshiya Sakata et al.; "DNA Sequencing Using Genetic Field Effect Transistor", Dai 65 Kai Oyo Butsuri Gakkai Gakujutsu Koenkai Koen Yokoshu, Sep. 1, 2004, No. 3, p. 1142.

Andrew Marshall et al., "DNA chips: An array of possibilities", Nature Biotechnology 1998, vol. 16, pp. 27&40.

Shigeori Takenaka et al., "DNA Sensing on a DNA Probe-Modified Electrode Using Ferrocenylnaphthalene Diimide as the Electrochemically Active Ligand", Analytical Chemistry 2000, vol. 72, pp. 1334-1341.

Minako Hijikata et al., "Identification of a Single Nucleotide Polymorphism in the MxA Gene Promoter (G/T at nt-88) Correlated with the Response of Hepatitis C Patients to Interferon", Intervirology, 2000, vol. 43, pp. 124-127.

E. Souteyrand et al., "Direct Detection of the Hybridization of Synthetic Homo-Oligomer DNA Sequences by Field Effect", J. Phys. Chem. B, 1997, 101, pp. 2980-2985.

Yining Shi et al., "Radial Capillary Array Electrophoresis Microplate and Scanner for High-Performance Nucleic Acid Analysis", Anal. Chem., 1999, vol. 71, pp. 5354-5361.

Translation of International Preliminary Report on Patentability mailed Mar. 29, 2007 of International Application No. PCT/JP2005/015522.

\* cited by examiner

Hybridization dCTP dATP dGTP dTTP dCTP

SAMPLE REAGENT

SIGNAL PROCESSING CIRCUIT

SEQUENCE LISTING

<160> NUMBER OF SEQ ID NOS: 13

<210> SEQ ID NO 1
<211> LENGTH: 11
<212> TYPE: DNA
<213> ORGANISM: Artificial
<220> FEATURE:
<223> OTHER INFORMATION: chemically synthesized

```
<400> SEQUENCE: 1
cgtcctctga a                                                          11

<210> SEQ ID NO 2
<211> LENGTH: 12
<212> TYPE: DNA
<213> ORGANISM: Artificial
<220> FEATURE:
<223> OTHER INFORMATION: chemically synthesized

<400> SEQUENCE: 2
cgtcctctga ac                                                         12

<210> SEQ ID NO 3
<211> LENGTH: 13
<212> TYPE: DNA
<213> ORGANISM: Artificial
<220> FEATURE:
<223> OTHER INFORMATION: chemically synthesized

<400> SEQUENCE: 3
cgtcctctga aca                                                        13

<210> SEQ ID NO 4
<211> LENGTH: 17
<212> TYPE: DNA
<213> ORGANISM: Artificial
<220> FEATURE:
<223> OTHER INFORMATION: chemically synthesized

<400> SEQUENCE: 4
cgtcctctga acaccc                                                     17

<210> SEQ ID NO 5
<211> LENGTH: 20
<212> TYPE: DNA
<213> ORGANISM: Artificial
<220> FEATURE:
<223> OTHER INFORMATION: chemically synthesized

<400> SEQUENCE: 5
agctggggtg ttcagaggac                                                 20

<210> SEQ ID NO 6
<211> LENGTH: 21
<212> TYPE: DNA
<213> ORGANISM: Artificial
<220> FEATURE:
<223> OTHER INFORMATION: chemically synthesized

<400> SEQUENCE: 6
agctggggtg ttcagaggac g                                               21

<210> SEQ ID NO 7
<211> LENGTH: 10
<212> TYPE: DNA
<213> ORGANISM: Artificial
<220> FEATURE:
<223> OTHER INFORMATION: chemically synthesized

<400> SEQUENCE: 7
caccccagtc                                                            10

<210> SEQ ID NO 8
<211> LENGTH: 17
```

-continued

```
<212> TYPE: DNA
<213> ORGANISM: Artificial
<220> FEATURE:
<223> OTHER INFORMATION: chemically synthesized

<400> SEQUENCE: 8
acgtgccccg gtagtgg                                                    17

<210> SEQ ID NO 9
<211> LENGTH: 17
<212> TYPE: DNA
<213> ORGANISM: Artificial
<220> FEATURE:
<223> OTHER INFORMATION: chemically synthesized

<400> SEQUENCE: 9
ccactaccgg ggcacgt                                                    17

<210> SEQ ID NO 10
<211> LENGTH: 21
<212> TYPE: DNA
<213> ORGANISM: Artificial
<220> FEATURE:
<223> OTHER INFORMATION: chemically synthesized

<400> SEQUENCE: 10
ctccacctgg cacgtatatc t                                               21

<210> SEQ ID NO 11
<211> LENGTH: 21
<212> TYPE: DNA
<213> ORGANISM: Artificial
<220> FEATURE:
<223> OTHER INFORMATION: chemically synthesized

<400> SEQUENCE: 11
agatatacgt gccaggtgga g                                               21

<210> SEQ ID NO 12
<211> LENGTH: 21
<212> TYPE: DNA
<213> ORGANISM: Artificial
<220> FEATURE:
<223> OTHER INFORMATION: chemically synthesized

<400> SEQUENCE: 12
cgactctcat gatcatagaa c                                               21

<210> SEQ ID NO 13
<211> LENGTH: 21
<212> TYPE: DNA
<213> ORGANISM: Artificial
<220> FEATURE:
<223> OTHER INFORMATION: chemically synthesized

<400> SEQUENCE: 13
gttctatgat catgagagtc g                                               21
```

METHOD OF ANALYZING DNA SEQUENCE USING FIELD-EFFECT DEVICE, AND BASE SEQUENCE ANALYZER

TECHNICAL FIELD

The present invention relates to fields of biotechnology such as genetic diagnosis, DNA sequence analyses, and polymorphism analyses, and, in particular, to a technology in the field of gene analyses. To be more specific, the present invention relates to a method for analyzing base sequence of nucleic acids using a field-effect device for gene detection that can analyze the base sequence of a nucleic acid without labeling with a fluorescent dye or radioisotope and an analyzer that uses the method.

BACKGROUND ART

Decoding of the entire base sequence of human genome is ended and decoding of genomic base sequences of other living organisms is under rapid progress. Under these circumstances, vast amounts of base sequence data are accumulating. Gene-related technologies are expected to dramatically develop in a wide range of fields including various disease diagnosis, drug development, breeding of agricultural crops, etc., as the functions of genes in vivo are elucidated on the basis of the genomic base sequence data.

In addition to the base sequence data, functional information of genes also forms the foundation for development of these new fields. As a technology for conducting functional analysis of genes on a large scale that enables development of gene examination, there have been developed electrophoresis, DNA chips and DNA microarrays (hereinafter generally referred to as DNA microarrays), and pyrosequencing, for example. Electrophoresis systems are distributed by Applied Biosystems and Agilent, for example. DNA microarrays are developed by Affymetrix and Nanogen, for example.

However, most of the existing electrophoresis systems and DNA microarrays are based on a fundamental principle of fluorescent detection; thus, it is necessary to give samples fluorescent labeling. This requires lasers and complex optical systems, which causes the system to be large and expensive. In particular, in the field of medicine, single nucleotide polymorphism (SNP) must be detected easily but with high accuracy in order to realize tailor-made medicine.

Most DNA microarrays now under development is based on a fundamental principle of detecting double-stranded DNAs by hybridization; thus, the selectivity of reaction is not very high and the accuracy needs improvement. Moreover, the base sequence analysis based on electrophoresis involves complicated preparation of samples and requires large equipment since high voltage and optical detection units are usually required. Thus, a technology that can satisfy the size, simplicity, economy, and high accuracy requirements has been demanded.

As means to overcome these problems, there are several reports of DNA microarrays of an electric current-detector type combined with redox labeling. Clinical Micro Sensors has developed a technology of detecting a target gene in which one end of a molecule called "molecular wire" is immobilized on a metal electrode and the other end is connected to a nucleic acid probe so that exchange of electrons between the metal electrode and the redox label based on the hybridization with the target gene is detected as a change in electric current (Nonpatent document 1).

TUM Laboratories has developed a technology of detecting hybridization through measuring the redox current at the metal electrode using ferrocenylnaphthalene diimide as a labeling agent having an electrochemical activity (Nonpatent document 2). Toshiba has developed a system of examining medicinal benefits for hepatitis C using DNA chips of a current-detecting type (Nonpatent document 3). According to this technology, neither expensive lasers nor complicated optical systems are required; thus, a small, simple system can be constructed. However, since its fundamental principle is to detect the oxidation-reduction reaction on the metal electrode, current caused by oxidation or reduction will flow if an oxidizing substance or a reducing substance (e.g., ascorbic acid) is present in the sample. This hinders gene detection and decreases detection accuracy. Moreover, along with the current measurement, electrode reaction progresses on the metal electrode. Since the electrode reaction is irreversible and non-equilibrium, corrosion of the electrode, generation of gasses, separation of immobilized nucleic acid, and degradation of stability of current measurement would result. Thus, detection accuracy is degraded especially when measurement is repeated.

There is also a report of an attempt to detect hybridization of DNAs using field-effect devices (Nonpatent document 4). This technology, which is based on the fact that DNA molecules have negative charges in solutions, detects change in electric charge caused by hybridization using the field effect. However, DNA probes formed on a substrate are inherently negatively charged; thus, the change in charge by hybridization with target DNAs is so small that it cannot be distinguished from nonspecific adsorption. Thus, in order for the technology to be suitable for gene examination, improvements in sensitivity and accuracy are necessary. Furthermore while detecting a minute difference (a difference of one base) between two genes is required in the case of single nucleotide polymorphism (SNP), the sensitivity and accuracy (selectivity) of this technology are unsatisfactory and detection is difficult. Moreover, according to a method based on a fundamental principle of hybridization only as in the case of DNA microarrays described above, it is impossible to analyze base sequence of target genes (DNA sequencing).

Electrophoresis technology is popular as a method for conducting DNA sequencing. A system for analyzing short sequences (short sequencing) downsized by forming migration paths on a glass or polymeric plate has been developed (Nonpatent document 5). However, the system requires application of high voltage and an optical system for fluorescence detection and is not different from conventional electrophoresis regarding the fundamental principle. Thus, problems of size, simplicity, economy, etc., still exist.

On the other hand, pyrosequencing is a detection technology utilizing chemical emission from enzymes caused by release of pyrophosphate that accompanies DNA elongation reaction. According to this technology, enzymes and reagents (dATP, dGTP, dCTP, and dTTP) are sequentially added and emission is detected to analyze the base sequences of DNAs. This method is relatively simple and suitable for small-size systems; however, the chemical reaction system is complex and parallel analysis of a large number of genes different from one another is difficult (Nonpatent document 6).

Several DNA detecting sensors utilizing the field effect have been reported. Eagle Research and Development, LLC forms micropores in a silicon substrate and fabricated a gate portion of a field-effect transistor on the inner sidewall of the micropore (patent document 1). Because the diameter of the micropore is small, a DNA molecule passing through the micropore passes through the vicinity of the gate portion. Since the DNA molecule has a negative charger the DNA molecule can be detected by the field-effect transistor. The distance between adjacent bases in the DNA molecule is 0.34 nm; thus, according to this method, it is difficult to analyze the base sequence by individually identifying the adjacent bases. Moreover, the document is silent as to the elongation reaction caused by addition of enzymes and substrates.

Hitachi discloses a DNA sensor that detects a target DNA using a field-effect transistor having a channel having a thin-line shape, in which a nucleic acid probe is immobilized on an insulating film surface on the channel and the change in conductivity of the channel caused by allowing a target DNA chain to flow along the thin-line channel is measured (patent document 2). This technology is also of a kind that detects a signal based on complementary binding of DNAs; thus, the base sequence cannot be analyzed. This known example also is silent as to elongation reaction caused by addition of enzymes and substrates.

Patent document 1: PCT Japanese Translation Patent Publication No. 2003-533676

Patent document 2: Japanese Unexamined Patent Application Publication No. 8-278281

Nonpatent document 1: Nature Biotechnology, vol. 16 (1998), p. 27, p. 40

Nonpatent document 2: Analytical Chemistry, 72 (2000) 1334

Nonpatent document 3: Intervirology, 43 (2000) 124-127

Nonpatent document 4: J. Phys. Chem. B 101 (1997) 2980-2985

Nonpatent document 5: Y. Shi et al., Anal. Chem., 71 (1999)

Nonpatent document 6: Ronagi, M.; Uhlen, M.; Nyren, P., Science, 1998, 281, 363-365

DISCLOSURE OF INVENTION

Problems to be Solved by Invention

Of the conventional technologies described above, the DNA microarrays require expensive, complex optical systems and have insufficient sensitivity and accuracy (selectivity) which render them unsuitable for detecting minute differences (a difference of one base) between two genes, such as in the case of single nuclectide polymorphism, due to deterioration of electrodes and a difference in dissociation temperature of DNAs. Thus, detection has been difficult. Furthermore, the electrophoresis technology has problems of size, simplicity, economy, etc., and the pyrosequencing technology has difficulty of parallel analysis of a plurality of genes.

Means for Solving the Problems

According to the present invention, a nucleic acid probe is immobilized at a gate portion of a field-effect transistor, and hybridization with a target DNA is conducted at the gate portion. Furthermore, an enzyme, i.e., a DNA polymerase, is added and dATP, dGTP, dCTP, and dTTP, which are its substrates, are sequentially added to induce elongation reaction. The change in electrical characteristic of the field-effect device, i.e., the change in threshold voltage or flat-band voltage, is detected each time the substrate is added. When a base complementary to the base of the target DNA is added, elongation reaction occurs due to the DNA polymerase and a polynucleotide is synthesized. Thus, the negative charge at the surface on which the nucleic acid probe is immobilized is increased. In contrast, when a base not complementary is added, no elongation reaction occurs and no change in charge is generated. Therefore, the base sequence of the target DNA can be analyzed by detecting an increase in negative charge on the basis of the substrate added.

The method for analyzing a DNA sequence according to the present invention is characterized in including:

(a) a step of immobilizing a single-strand nucleic acid probe at a gate portion of a field-effect device and introducing a sample solution containing at least one type of nucleic acid into a sample solution well in the gate portion to conduct hybridization with the single-strand nucleic acid probe;

(b) a step of introducing a washing liquid into the sample solution well to remove unreacted nucleic acid from the sample solution well;

(c) a stop of introducing enzyme Taq polymerase and one of substrates, dATP, dGTP, dCTP, and dTTP to induce elongation reaction;

(d) a step of introducing a washing liquid into the sample solution well to remove the unreacted enzyme and substrate from the sample solution well;

(e) a step of introducing a buffer solution into the sample solution well to measure changes in threshold voltage or flat-band voltage of the field-effect device; and (f) a step of returning to step (c), introducing enzyme Taq polymerase and a different one of the substrates (dATP, dGTP, dCTP, and dTTP) into the sample solution well to induce second elongation reaction and measuring changes in threshold voltage or flat-band voltage of the field-effect device.

In order to principally determine whether a base is A, G, C, or T, four types of bases, dATP, dGTP, dCTP, and dTTP are added one by one. In order to determine the type of a base next to it, four types of bases, dATP, dGTP, dCTP, and dTTP are again added one by one. Thus, in order to determine the DNA sequence consisting of 10 bases, addition of substrate is conducted at most 40 times. How many times the step of adding the substrate is repeated is determined based on the base-length of the DNA to be analyzed.

In order to induce hybridization and elongation reaction at high accuracy on the field-effect device for gene detection according to the present invention, the reaction temperature must be controlled to an optimum value. The field-effect device is characterized in that a temperature sensor and a heater are integrated therein.

The present invention is characterized in the use of a flow cell in which a field-effect device for gene detection is mounted on a print circuit board and electrically connected to the print circuit board through wires; the print circuit board is provided with pins so that the print circuit board is connected to a signal processing circuit; a sample solution is supplied through a channel to a sample solution well provided in a gate portion of the field-effect device; and the wires are protected with a protective cap so that the sample solution does not contact the wires serving as signal lines.

Advantages

The present invention enabled DNA sequence analysis without labeling by combining a field-effect device, hybridization, and following elongation reaction. The present invention does not require expensive lasers or complex optical systems and can analyze DNA sequence without labeling with fluorescent substance or radioisotopes. Thus, a small gene sequence analyzing system can be provided.

BEST MODE FOR CARRYING OUT THE INVENTION

In the present invention, a nucleic acid probe is immobilized at a gate portion of a field-effect device, i.e., a field-effect transistor or field-effect capacitor, so as to allow hybridization of a target gene and the gate portion, and an enzyme and substrates, dATP, dGTP, dCTP, and dTTP, are sequentially added to induce elongation reaction. The increase in negative charge that has occurred by addition at the surface on which the nucleic acid probe is immobilized is detected on the basis of the field effect.

The present invention will now be described in further detail with reference to the attached drawings. In the drawings below, the sections having the same functions are represented by the same reference numerals. The method for analyzing DNA sequences is described with reference to FIGS. 1 to 6.

FIG. 1(a) is a cross-sectional view describing an example of a field-effect device for gene detection according to the present invention. A P-well 2 is formed in a silicon substrate 1, and n-type regions 3, which function as a source and a drain, are formed in the P-well 2. A lower insulating film 4 is formed over the P-well 2. The lower insulating film 4 preferably contains silicon dioxide ($SiO_2$). Since silicon dioxide hydrates by contacting an aqueous solution and therefore exhibits degraded insulating ability, it is preferable to form a two-layer insulating film by forming an upper insulating film 5 with good water resistance to maintain satisfactory electrical characteristics on the silicon surface. The upper insulating film 5 may contain one or more materials, such as silicon nitride (SiN or $Si_3N_4$), aluminum oxide ($Al_2O_3$), and tantalum oxide ($Ta_2O_5$)

In order to accurately monitor reaction temperature of the nucleic acid, an n-type region 9 is formed in the P-well 2 and used as a temperature sensor. An electrode is formed in each of the P-well 2 and the n-type region 9 to form a pn-junction diode, and the temperature characteristic of the voltage-current characteristic of the pn-junction diode is used so that the n-type region 9 can serve as the temperature sensor. That is, a constant voltage of preferably 0.6 V or more is applied to the pn-junction diode and the current is measured. A calibration curve is prepared in advance by measuring the current value with respect to temperature change, and the temperature is determined from the calibration curve and the observed current value.

By patterning the n-type region or the metal thin film to render a line shape, a heater can be integrally formed. By supplying a current to the n-type region or the metal thin film, heat can be generated and the temperature can be increased. By combining the temperature sensor and the heater, the temperature of the plate on which the field-effect transistor is formed can be controlled to an optimum value, and the accuracy of hybridization and elongation reaction can be improved.

The region between the n-type regions 3 is the gate portion. FIG. 1(b) shows an enlarged view of the gate portion. Silicon oxide 7 and phosphoric glass (PSG) 8 are sequentially stacked on the surface in the region other than the gate portion so as to protect the oxide silicon 7 portion from the solution. The thickness of the silicon oxide 7 and the phosphoric glass (PSG) is usually about 500 to 2000 nm, which is larger than that of the insulating film of the gate portion (silicon oxide and silicon nitride: 100 to 200 nm). As shown in FIG. 1(b), because the silicon oxide 7 and the phosphoric glass (PSG) 8 are thick, a sidewall is formed to surround the gate portion and a sample solution well structure which can retain a sample solution is thereby formed. Nucleic acid probes 6 are immobilized at this gate portion. The immobilization is preferably conducted on the surface of the insulating film of the gate portion (referred to as "gate insulating film" hereinafter), as shown in FIG. 1(b). However, it is possible to immobilize them on the sidewall of the silicon oxide 7 and the phosphoric glass 8 near the gate portion.

A target gene is hybridized with the nucleic acid probe 6 immobilized on the sidewall of the sample solution well structure, and a Taq DNA polymerase and a substrate are introduced to the sample solution well to induce elongation reaction. As a result, DNAs are synthesized along the surface in the lateral direction in parallel to the surface of the gate insulating film. Threshold voltages change by the electrostatic interaction with the charged particles (electrons) in the P-well 2. Thus, synthesis of DNAs in a direction parallel to the gate insulating film surface, which keeps the distance between the DNA and the electrons constant, helps maintain the electrostatic interaction constant. Thus, the base sequence of a gene having a large base length can be analyzed.

In contrast, when the nucleic acid probes immobilized on the gate insulating film surface and extending in the vertical direction are used, the distance to the electrons on the surface of the P-well, i.e., the surface of the gate insulating film, increases with the progress of synthesis of the DNAs by elongation reaction. Therefore, the electrostatic interaction decreases as the base length synthesized increases, and there is a limit to the detectable base length. Thus, in analyzing the base sequence of a target gene having a large base length, it is important that the elongation reaction in the lateral direction be used.

In immobilizing nucleic acid probes chemically modified with a thiol group, a gold thin film is formed on the sidewall of the sample solution well structure or on the gate insulating film so that the nucleic acid probes are immobilized by the attraction between the thiol group and gold. In immobilizing nucleic acid probes chemically modified with biotin, streptavidin is introduced into the sidewall of the gate insulating film surface or sidewall of the sample solution well structure so that the nucleic acid probes are immobilized by the attraction between the biotin and streptavidin. In actual immobilization, a solution containing nucleic acid probes is dropped or spotted into a sample solution well only and is chemically reacted with functional groups on the gate insulating film or side wall of the sample solution well to immobilize the nucleic acid probes.

A field-effect device for gene detection is disposed in a flow cell, and a sample solution is introduced to a sample solution well. A reference electrode is disposed downstream of the field-effect device for gene detection, and gate voltage is applied whenever needed.

In particular, at least two field-effect transistors are used. One is used as a field-effect device for gene detection and the other is used as a reference field-effect device to compensate the change in light or temperature and change in output of the transistor by non-specific adsorption. In order to conduct parallel analysis of a plurality of genes, the number of the transistors needs to be equal to or higher than the number of types of DNAs to be analyzed. Each nucleic acid probe 6 is an oligonucleotide or a fragment of cDNA and is usually constituted from 300 or less bases. When the oligonucleotide is used, a fragment of nucleic acid having 80 bases or fewer is preferable.

In order to immobilize the nucleic acid probe, one end of the nucleic acid probe is chemically modified with an amino group (NH₂ group), a thiol group (SH group), biotin, or the like. In using a nucleic acid probe chemically modified with an amino group, the surface of the gate insulating film and the sidewall of the sample solution well structure are chemically modified with aminopropylethoxysilane, polylysine, or the like to introduce an amino group to the gate insulating film surface or the sidewall surface of the sample solution well structure. Subsequently, reaction with glutaric aldehyde or phenylene diisocyanate (PDC) is conducted to immobilize nucleic acid probes chemically modified with amino groups on the gate insulating film surface or the sidewall of the sample solution well structure.

When a large number genes including a target gene to be measured are present in a sample solution and when a nucleic acid probe having a complementary base sequence to the target gene is immobilized on the gate insulating film or the sidewall surface of the sample solution well structure of the field-effect device for gene detection, the target gene hybridizes with the nucleic acid probe under appropriate reaction conditions and the target gene and the nucleic acid probe form a double strand. Here, the base sequence of the nucleic acid probe is previously designed to be shorter than the base length of the target gene in such a way that the hybridization is conducted at a location adjacent to the portion that needs base sequence analysis.

In order to analyze the base sequence, a DNA polymerase and substrates, dATP, dGTS, dCTS, and dTTP, are sequentially added after the hybridization to induce elongation reaction, and the change in electrical characteristic (threshold voltage) is measured for every elongation reaction with the individual substrate. Since DNAs have a negative charge in aqueous solutions, elongation reaction occurs and polynucleotides are synthesized if the substrate is complementary to the base sequence of the target DNA. As a result, the negative charge on the gate insulating film surface or the sidewall surface of the sample solution well structure is increased, and that increase can be detected as a change in threshold voltage. By checking addition of which substrate has resulted in a signal of change in threshold voltage, the base sequence of the target gene can be analyzed.

Specific description will now be provided below with reference to FIG. 2. By using the base sequence of a portion of factor VII gene, which is one of blood coagulation genes, a base sequence of a nucleic acid probe is designed as below.
<Nucleic acid probe base sequence: 5'-CGTCCTCTGAA-3'>(SEQ ID NO: 1).

At the 5'-terminus of the nucleic acid probe, an amino group is introduced so that the probe is immobilized on the gate insulating film surface. The gate insulating film of the field-effect transistor of this embodiment contains silicon nitride, and the surface thereof is chemically modified with γ-aminopropyltriethoxysilane to introduce an amino group in the silicon nitride surface. The amino group of the nucleic acid probe and the amino group of silicon nitride are, for example, reacted with a bifunctional reagent, such as glutaric aldehyde, to form binding by a Schiff base and to thereby immobilize the nucleic acid probe on the silicon nitride surface.

As shown in FIG. 2, the factor VII gene nucleic acid probe 6 consisting of 11 bases (SEQ ID NO: 1) was immobilized on the gate insulating film surface of the field-effect transistor and reacted with a sample containing factor VII gene 10 consisting of 21 bases (SEQ ID NO: 5) previously amplified by polymerase chain reaction (PCR). The sample was retained in a container as a sample solution.

The human genome was extracted from white blood cells in blood and 21-base region including the factor VII gene segment described above was amplified to form the sample solution. The sample solution was then introduced to the gate portion of the field-effect transistor for gene detection on which the nucleic acid probe is immobilized, and hybridization was conducted at 45° C. for 8 hours. After the hybridization, washing with a buffer solution was conducted to remove the unreacted sample from the gate portion. FIG. 2(a) shows the state after the hybridization of the factor VII gene nucleic acid probe (SEQ ID NO: 1) with the factor VII gene (SEQ ID NO: 5), which is the target gene.

Next, the enzyme, Taq DNA polymerase and substrates, dATP, dGTP, dCTP, and dTTP are sequentially added. First, a field-effect transistor for gene detection was placed in a buffer solution, and the temperature was set to 74° C. using the temperature sensor and the heater integrated in the field-effect device. The Taq DNA polymerase and the substrate, dCTP were added to the buffer solution to carry out elongation reaction on the gate insulating film.

Then, as shown in FIG. 2(b), because cytosine (C) is complementary to the base guanine (G) on the target gene adjacent to the 3'-terminus of the nucleic acid probe, elongation reaction occurs, resulting in synthesis of one cytosine (SEQ ID NO: 2). After the elongation reaction, the enzyme, Taq DNA polymerase and the substrate dCTP were washed away from the gate, and a phosphoric acid buffer solution having a pH of 6.86 was introduced on the gate insulating film to measure changes in threshold voltage. As a result, the threshold voltage was increased by 4 mV from before the elongation reaction. The shift of the threshold voltage in the positive direction indicates that a negative charge was generated on the gate surface. It can be understood from this that synthesis of one base caused by the elongation reaction was detectable as a change in threshold voltage.

Subsequently, a buffer solution for elongation reaction was introduced on the gate insulating film to replace the phosphoric acid buffer solution, and the temperature was set to 74° C. A Taq DNA polymerase and the substrate dATP were added to induce second elongation reaction on the gate insulating film. As shown in FIG. 2(c), the next adjacent base on the target gene was thymine (T). Since adenine (A) added was complementary to thymine (T), elongation reaction occurred and one adenine was synthesized (SEQ ID NO: 3).

After this elongation reaction, the enzyme, Taq DNA polymerase and the substrate dATP were washed away from the gate insulating film, and a phosphoric acid buffer solution having a pH of 6.86 was introduced on the gate insulating film to measure changes in threshold voltage. As a result, the threshold voltage was further increased by 4 mV from before the second elongation reaction. The elongation reaction occurred by addition of one base complementary to the base sequence of the target gene, and a signal was thereby obtained as a change in threshold voltage.

The above operation is repeated. The gate insulating film surface was washed, and a buffer solution was introduced. The temperature was set to 74° C., and the Taq DNA polymerase and the substrate dGTP were added. As shown in FIG. 2(d), the next adjacent base on the target gene is guanine (G), which is not complementary to guanine (G). Thus, elongation reaction does not occur, and the threshold voltage remains unchanged.

After washing, the Taq DNA polymerase and the substrate dTTP were added. As shown in FIG. 2(e), the next base to be analyzed on the target gene is guanine (G). Since guanine (G) is not complementary to thymine (T) added, elongation reaction does not occur, and the threshold voltage remains unchanged. Subsequently, the process returned to the beginning of the cycle of adding four bases, and the Taq DNA polymerase and the substrate dCTP were added.

As shown in FIG. 2(f), the next base to be analyzed on the target gene is guanine (S). Since it is complementary to cytosine (C) added, elongation reaction occurs, and cytosine is synthesized. As shown in FIG. 2(f), four guanines were sequentially aligned, and four cytosines were synthesized (SEQ ID NO: 4). This resulted in a large change in threshold voltage, i.e., a change of 10 mV.

In the process of analyzing the base sequence described above, the relationship between the base added and changes in threshold voltage is as shown in FIG. 3. By sequentially adding the DNA polymerase and substrates, dCTP, dATP, dGTP, and dTTP and measuring the presence or absence of a signal of change in threshold voltage, the base sequence of the target gene (SEQ ID NO: 6) can be analyzed. As shown in FIG. 2(f), when the same bases are successively aligned, the number of bases can be fundamentally derived from the magnitude of the shift of threshold voltage. Beginning with the nucleic acid probe (SEQ ID NO: 1), elongation occurs by which additional bases are synthesized (SEQ ID NO: 7).

As in this embodiment, according to the DNA sequence analysis using the field-effect transistor and elongation reaction, the progress of reaction can be constantly monitored by detecting the potential change during the processes of introduction of a sample on the gate insulating film, hybridization, and elongation reaction. Thus, completion of the reaction can be detected from the change in potential, and the base sequence analysis can be conducted efficiently. Moreover, according to the present invention, since the synthesis of the base caused by elongation reaction is detected as an increase in electrical charge, base sequence can be analyzed without labeling the target gene with a fluorescent dye, radioisotope, or the like.

FIG. 4 is a diagram for explaining an example of a measuring instrument using the field-effect device for gene detection according to the present invention. At least two types of nucleic acid probes and two field-effect devices for gene detection are mounted on a flow cell 11 and connected to a channel 12. A nucleic acid probe having a sequence complementary to the base sequence of a gene analyzed is immobilized on the surface of the gate insulating film of one of the field-effect devices while no probe is immobilized on the surface of the gate insulating film of the other field-effect device so that this device can be used as the reference field-effect device. By measuring the difference between output signals of the field effect devices, the change in threshold voltage caused by elongation reaction is measured. By conducting differential measurement, changes in output signals caused by light or temperature changes and common changes in output derived by nonspecific adsorption or ion concentration changes can be set off, and only the changes caused by elongation reaction can be measured with high precision.

A buffer solution 13 and a washing liquid 14 are connected to the channel 12 via a valve 15. The buffer solution and the washing liquid can be introduced to the flow cell 11 by driving a pump 16. The sample, the enzyme, Taq polymerase for elongation reaction, and the substrates, dATP, dGTP, dCTP, and dTTP are dispensed into the valve 15 with a dispensing burette 17 and introduced into the flow cell 11 so that they can be reacted with the field-effect device for gene detection.

Upon completion of the reaction, the used liquid is sent to a waste liquid bottle 18 by the pump 16. A Ag—AgCl electrode is used as a reference electrode 19, and a 3M KCl solution 20 is passed through the electrode and connected to the channel 12 downstream of the flow cell 11 to form a liquid-liquid junction 21 and to thereby be electrically connected to the field-effect device for gene detection. On the basis of the output of the threshold voltage of the field-effect device for gene detection after the reaction, a signal processing circuit 22 conducts denoizing, calculation of the difference in threshold voltage between before and after the addition of substrates, comparison of the difference in threshold voltage with the noise, calculation of the number of bases on the basis of the magnitude of the change in threshold voltage, determination of base sequence on the basis of the type of base added and the magnitude of change in threshold voltage, etc.

FIG. 5 shows the structure of the flow cell 11. A field-effect device 24 for gene detection is mounted on a print circuit board 23 in the flow cell 11 and is electrically coupled with the print circuit board 23 via wires 25. The print circuit board 23 is provided with pins 26 that connect the print circuit board 23 to the signal processing circuit 22. The sample solution is introduced to the field-effect device 24 for gene detection through the channel 12. The wire portions are protected with a protection cap 27 so that the sample solution does not contact the wires 25 serving as signal lines. The material of the protection cap 27 is preferably acryl, polypropylene, polycarbonate, or the like.

The field-effect device measuring system for gene detection having this structure can automatically and continuously process a large number of samples and is effective for measurement at high throughput. When the base sequence analysis of the factor VII gene described in the above embodiment is conducted with the measurement system shown in FIG. 4, the measurement is conducted according to the following steps:

(1) Introduce the washing liquid 14 into the flow cell 11.

(2) Introduce the buffer solution 13 to the flow cell 11 (replace the washing liquid 14).

(3) Dispense the sample into the valve 15 and introduce the sample to the flow cell 11.

(4) Conduct hybridization in the flow cell 11.

(5) Introduce the buffer solution 13 into the flow cell 11 to remove unreacted sample.

(6) Measure the threshold voltage output value of each field-effect device for gene detection.

(7) Set the temperature of the field-effect device to the optimum temperature for Taq DNA polymerase (74° C.).

(8) Introduce enzyme Taq DNA polymerase and one of substrates, dCTP, dATF, dGTP, and dTTP into the flow cell 11 to induce elongation reaction.

(9) Introduce the buffer solution 13 into the flow cell 11 to remove unreacted enzyme and substrate.

(10) Measure the threshold voltage output value of each field-effect device for gene detection.

(11) Return to step (7). Repeat elongation reaction and threshold voltage measurement with a different substrate.

The measurement sequence is shown in FIG. 6. In the diagram, arrows each indicate a timing for reading the output potential.

EXAMPLE 1

The base sequence of the R353Q region of a blood coagulation factor, factor VII gene (SEQ ID NO: 8) was analyzed according to the process of the present invention. A nine-base long oligonucleotide probe was immobilized on the gate insulating film of the gene transistor. After hybridization with the target DNA, enzyme, Taq DNA polymerase and substrates, dATP, dGTP, dCTP, and dTTP were sequentially added, resulting in SEQ ID NO: 9. The observed threshold voltages of the gene transistor after addition of each substrate are shown in FIG. 7. FIG. 7 shows that the threshold voltage changes with addition of complementary bases, C, C, A, C, G, and T to the base sequence of the target DNA. FIG. 7 also shows that a threshold voltage change about three times greater in magnitude is observed by addition of G for the sequence having three cytosines in a row. In this manner, the base sequence of the R353Q region of the factor VII gene can be read.

EXAMPLES 2 AND 3

The base sequences of C282Y region (Example 2) (SEQ ID NO: 10) and H63D region (Example 3) (SEQ ID NO: 12) of a hereditary hemochromatosis gene were analyzed as in Example 1. The results are shown in FIGS. 8 and 9. In this example also, dATP, dGTP, dCTP, and dTTP were sequentially added, resulting in SEQ ID NO: 11 and SEQ ID NO: 12, respectively. Changes in threshold voltage were observed if the substrate was complementary to the base sequence of the target DNA. If not, no change in threshold voltage was observed. Moreover, when the same bases existed two in a row, a larger change in threshold voltage was observed compared with the case of only one base. Thus, the base sequence of the DNA can be analyzed without labeling according to the method of the present invention.

INDUSTRIAL APPLICABILITY

The present invention provides a field-effect device for gene detection which can examine genes with high precision while realizing an inexpensive system, a method for analyzing DNA sequence using the field-effect device, and an analytic system.

BRIEF DESCRIPTION OF THE DRAWINGS

FIG. 2 is a diagram for explaining the fundamental principle of DNA sequence analysis using the field-effect device for gene detection of the present invention.

In FIG. 3, SEQ ID NO: 1, SEQ ID NO: 6 and SEQ ID NO: 7 are illustrated.

In FIG. 7, SEQ ID NO: 8 and SEQ ID NO: 9 are illustrated.

In FIG. 8, SEQ ID NO: 10 and SEQ ID NO: 11 are illustrated.

In FIG. 9, SEQ ID NO: 12 and SEQ ID NO: 13 are illustrated.

REFERENCE NUMERALS

Figure 1A:
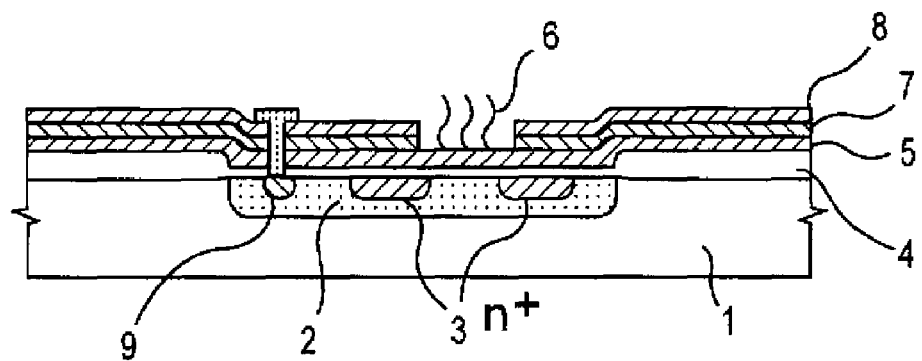
FIG. 1(a) is a schematic cross-sectional view explaining an example of a field-effect device for gene detection according to the present invention.
Figure 1B:
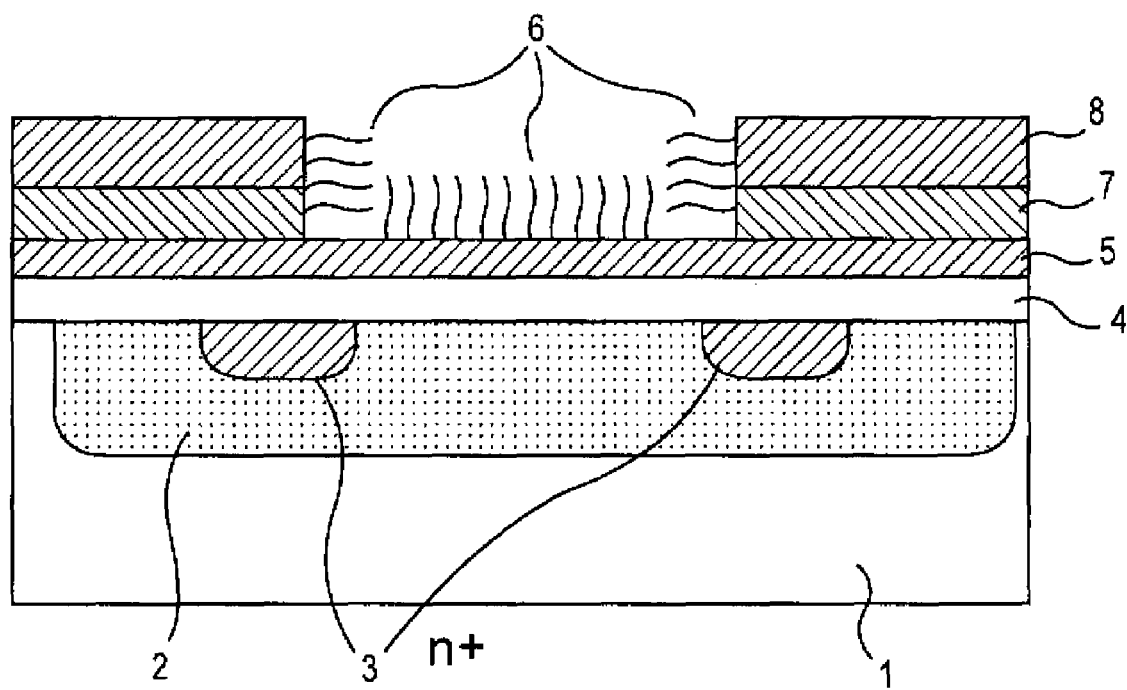
FIG. 1(b) is an enlarged view of a gate portion of the device.
Figure 2A:
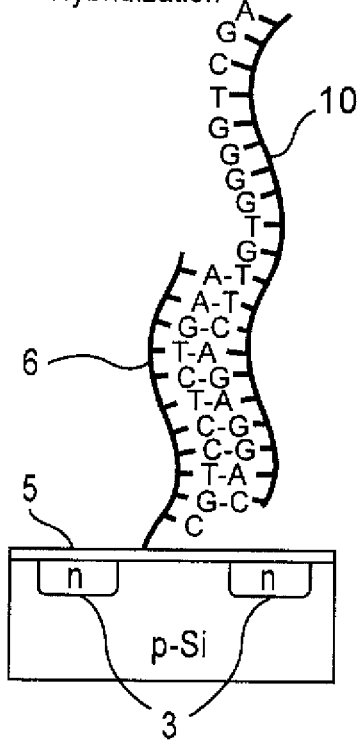
In FIG. 2(a), SEQ ID NO: 1 and SEQ ID NO: 5 are illustrated.
Figure 2B:
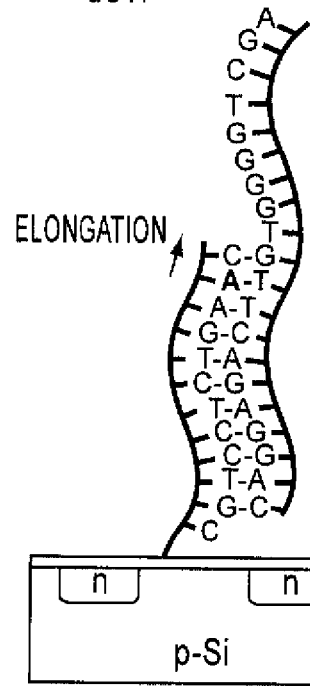
In FIG. 2(b), SEQ ID NO: 2 and SEQ ID NO: 5 are illustrated.
Figure 2C:
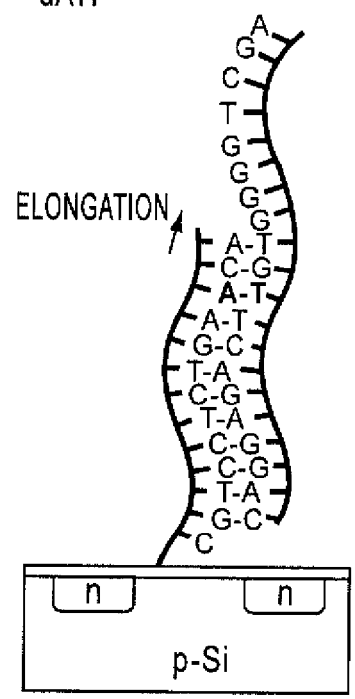
In FIG. 2(c), SEQ ID NO: 3 and SEQ ID NO: 5 are illustrated.
Figure 2D:
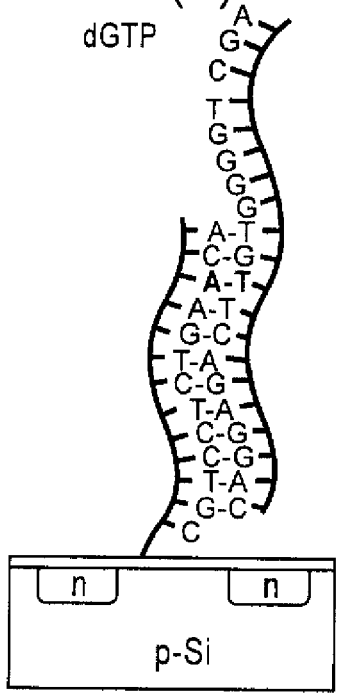
In FIG. 2(d), SEQ ID NO: 3 and SEQ ID NO: 5 are illustrated.
Figure 2E:
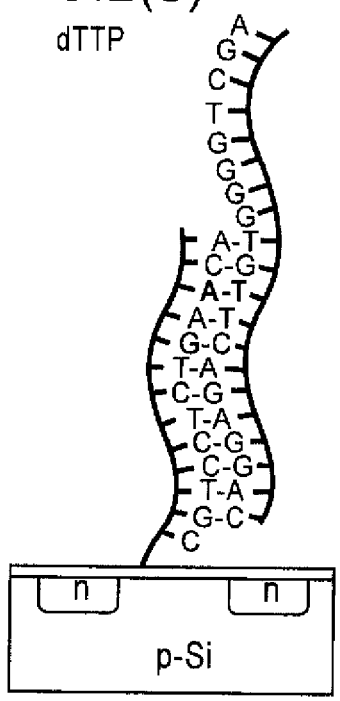
In FIG. 2(e), SEQ ID NO: 3 and SEQ ID NO: 5 are illustrated.
Figure 2F:
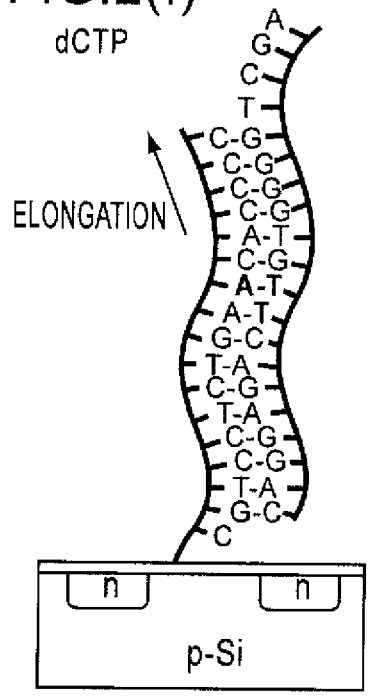
In FIG. 2(f), SEQ ID NO: 4 and SEQ ID NO: 5 are illustrated.
Figure 3:
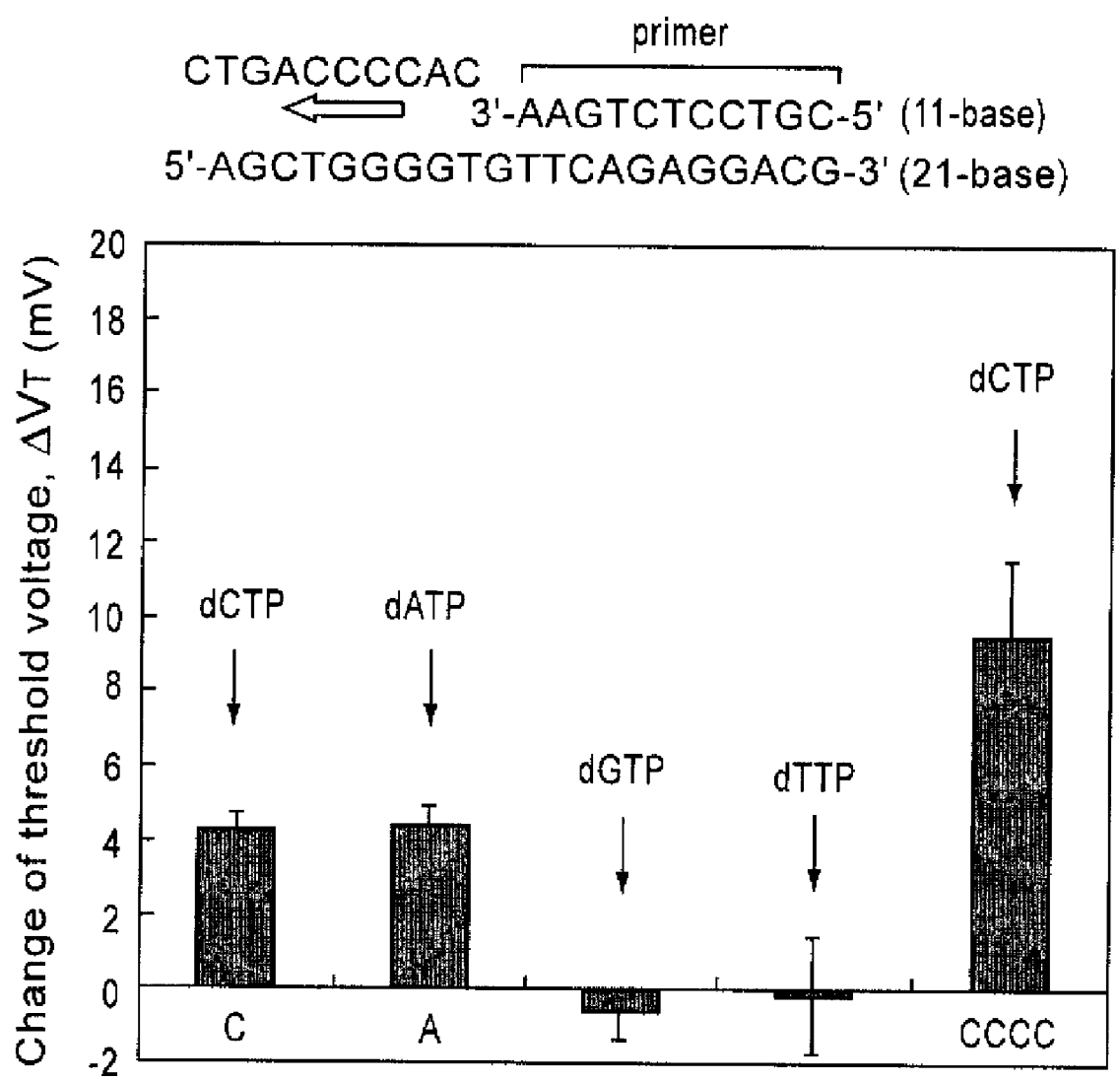
FIG. 3 is a graph for explaining the results of the DNA sequence analysis using the field-effect-device for gene detection according to the present invention.
Figure 4:
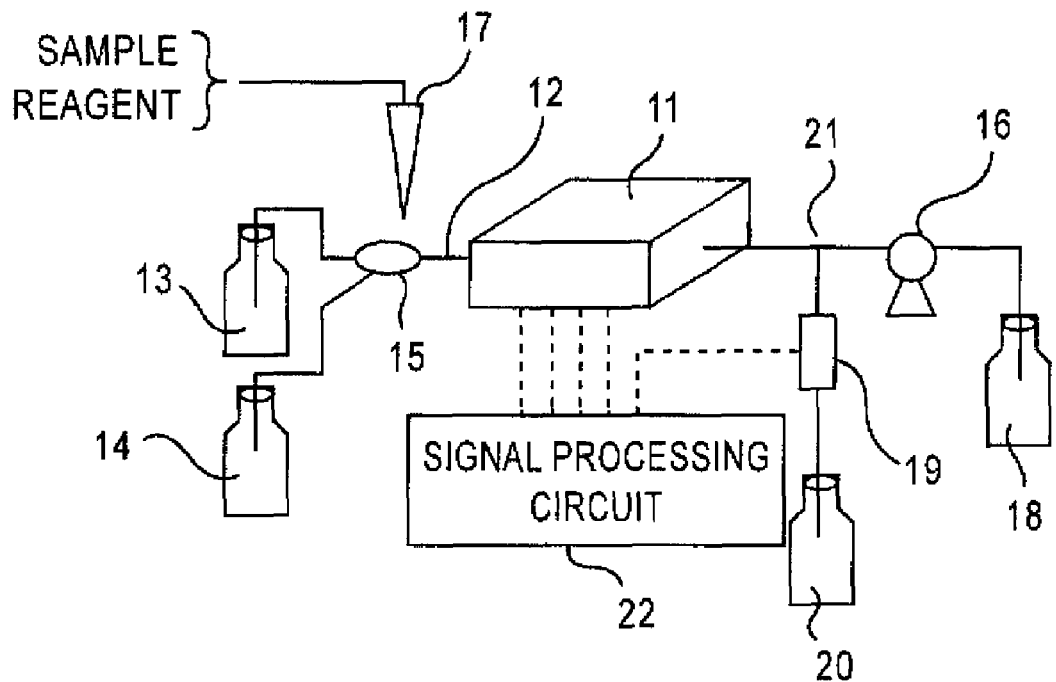
FIG. 4 is a diagram for explaining an example configuration of a measurement system using the field-effect device for gene detection of the present invention.
Figure 5:
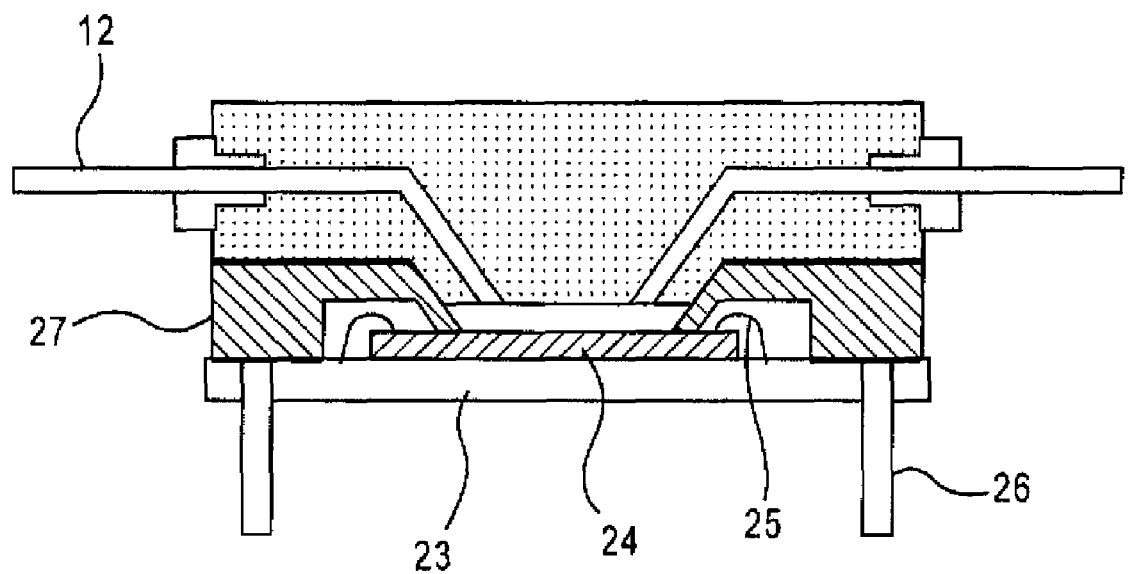
FIG. 5 is a schematic cross-sectional view of a flow cell on which the field-effect device for gene detection of the present invention is mounted.
Figure 6:
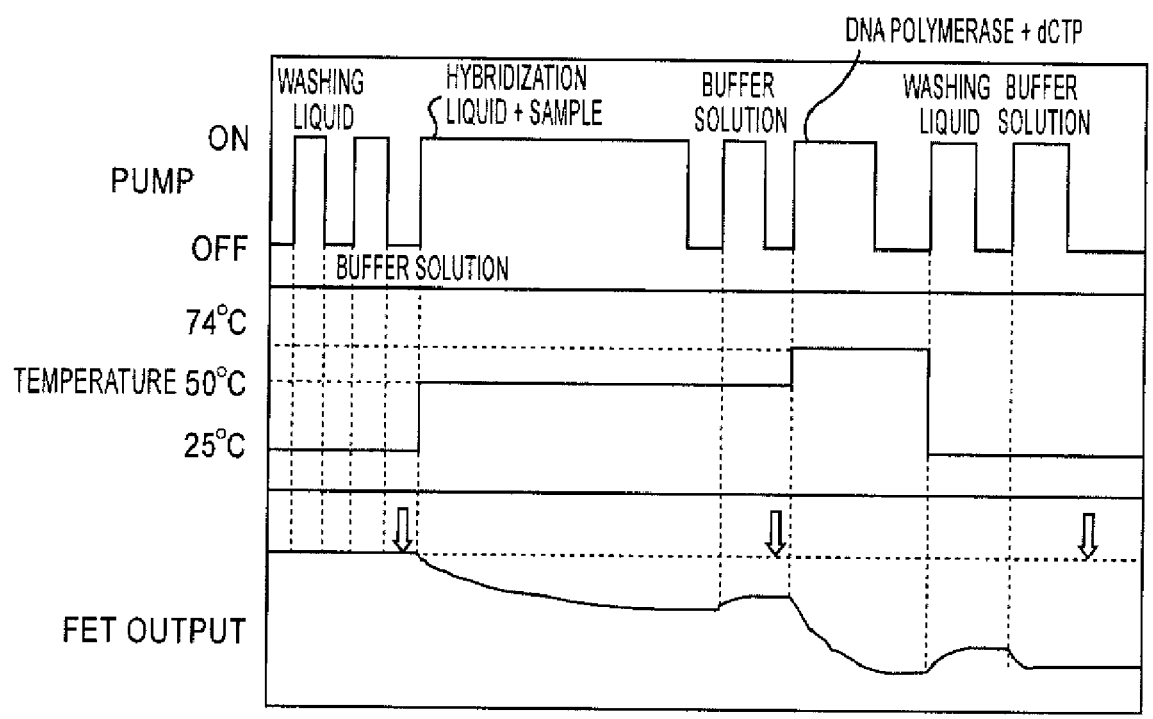
FIG. 6 is a diagram explaining a measurement sequence using the field-effect device for gene detection of the present invention.
Figure 7:
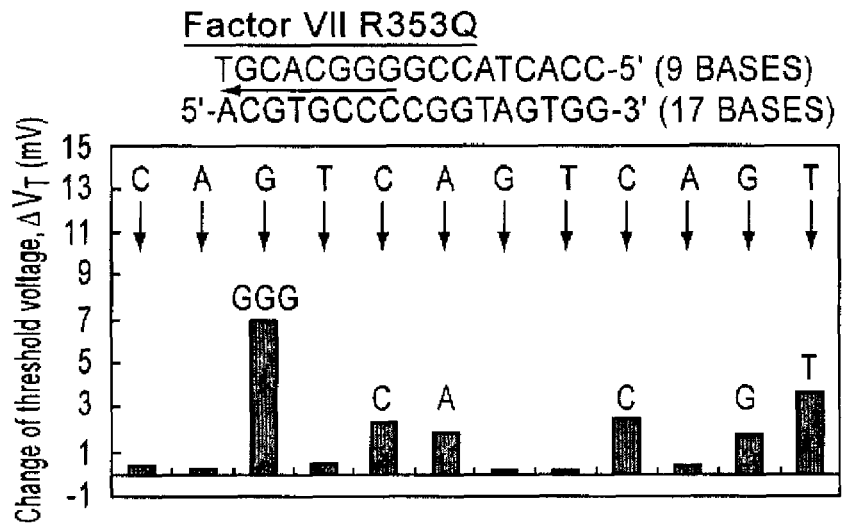
FIG. 7 is a diagram for explaining the results of base sequence analysis according to Example 1.
Figure 8:
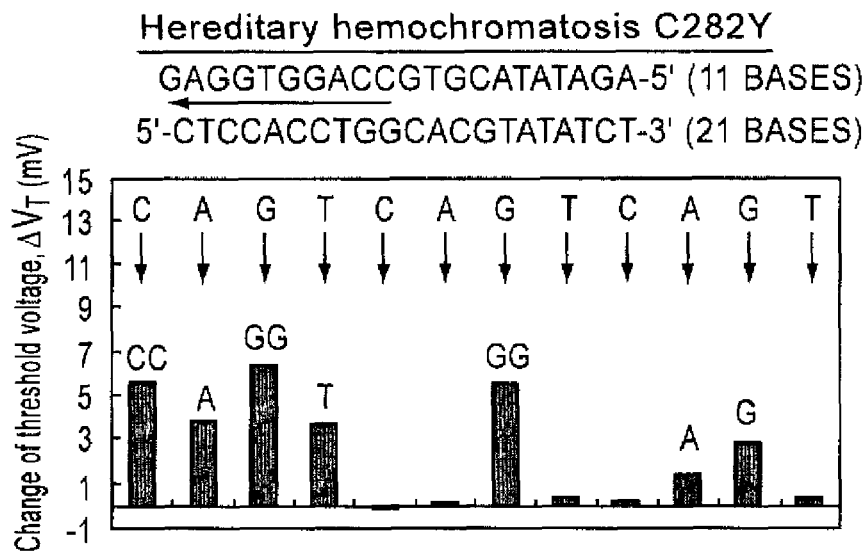
FIG. 8 is a diagram for explaining the results of base sequence analysis according to Example 2.
Figure 9:
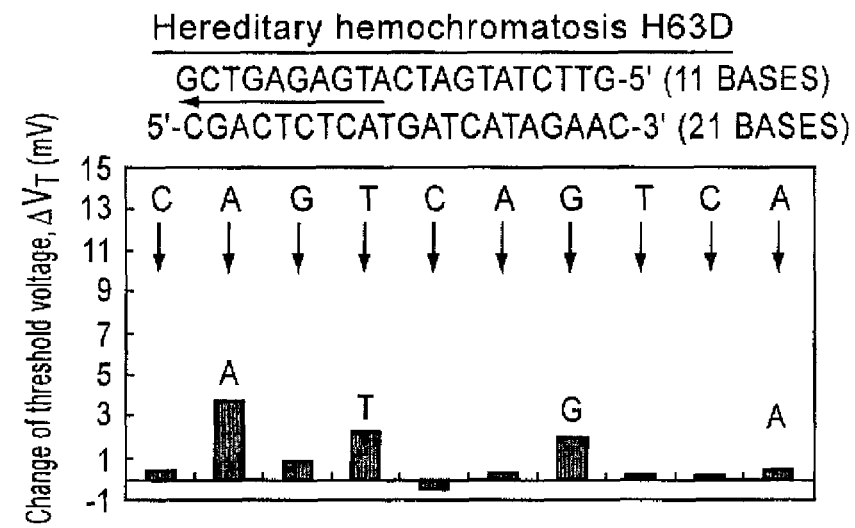
FIG. 9 is a diagram for explaining the results of base sequence analysis according to Example 3.

1: silicon substrate
2: P-well
3: n-type region
4: silicon dioxide
5: silicon nitride
6: nucleic acid probe
7: silicon dioxide
8: phosphoric glass
9: n-type region (temperature sensor)
11: flow cell
12: channel
13: buffer solution
14: washing liquid
15: valve
16: pump
17: dispenser
18: waste liquid bottle
19: reference electrode
20: 3M KCl solution
21: liquid-liquid junction
22: signal processing circuit
23: print circuit board
24: field-effect device for gene detection
25: wire
26: pin
27: protective cap

The invention claimed is:

1. A method for analyzing a base sequence, comprising:
 (a) immobilizing a single-strand nucleic acid probe at a gate portion of a field-effect device and introducing a sample solution containing at least one type of nucleic acid into a sample solution well in the gate portion to conduct hybridization with the single-strand nucleic acid probe;
 (b) introducing a washing liquid into the sample solution well to remove unreacted nucleic acid from the sample solution well;
 (c) introducing enzyme Taq polymerase and one of substrates, dATP, dGTP, dCTP, and dTTP to induce elongation reaction;
 (d) introducing a washing liquid into the sample solution well to remove the unreacted enzyme and substrate from the sample solution well;
 (e) introducing a buffer solution into the sample solution well to measure changes in threshold voltage or flat-band voltage of the field-effect device;
 (f) returning to said step (c), introducing enzyme Taq polymerase and a different one of the substrates (dATP, dGTP, dCTP, and dTTP) into the sample solution well to induce second elongation reaction and measuring changes in threshold voltage or flat-band voltage of the field-effect device, and
 (g) determining a base sequence based on the changes in threshold voltage or flat-band voltage.

2. A base sequence analyzer with a flow cell to mount a field-effect device for use in the method according to claim 1, comprising:
 a printed circuit board including a printed circuit and connecting terminals;
 a field-effect device for gene detection mounted on the printed circuit board and electrically connected to the printed circuit with conducting wires;
 a signal processing circuit electrically connected to the connecting terminals of the printed circuit board;
 a sample solution well provided in a gate portion of the field-effect device; and
 a protective cap covering one or more of the conducting wires serving as signal lines so that the sample solution does not contact the conducting wires.

3. The base sequence analyzer according to claim 2, further comprising a temperature sensor and a heater integrated in the field-effect device.

4. The method for analyzing a base sequence according to claim 1, wherein the field-effect device is a field-effect transistor or a field-effect capacitor.

5. The method for analyzing a base sequence according to claim 1, wherein a field-effect device in which a temperature sensor is integrated is used.

* * * * *